(12) United States Patent
Schmittling et al.

(10) Patent No.: US 8,900,816 B2
(45) Date of Patent: Dec. 2, 2014

(54) ASSAY FOR ANTI-EGFRVIII ANTIBODIES

(75) Inventors: Robert J. Schmittling, Hillsborough, NC (US); Gary E. Archer, Hillsborough, NC (US); John H. Sampson, Durham, NC (US); Darell D. Bigner, Mebane, NC (US)

(73) Assignee: Duke University, Durham, NC (US)

( * ) Notice: Subject to any disclaimer, the term of this patent is extended or adjusted under 35 U.S.C. 154(b) by 790 days.

(21) Appl. No.: 12/669,374

(22) PCT Filed: Jul. 21, 2008

(86) PCT No.: PCT/US2008/070637
§ 371 (c)(1),
(2), (4) Date: Jun. 9, 2010

(87) PCT Pub. No.: WO2009/012488
PCT Pub. Date: Jan. 22, 2009

(65) Prior Publication Data
US 2012/0115739 A1    May 10, 2012

Related U.S. Application Data

(60) Provisional application No. 60/950,800, filed on Jul. 19, 2007.

(51) Int. Cl.
*G01N 33/537* (2006.01)
*G01N 33/571* (2006.01)
*G01N 33/574* (2006.01)

(52) U.S. Cl.
CPC .... *G01N 33/57488* (2013.01); *G01N 2333/485* (2013.01)
USPC ........... 435/7.1; 435/7.22; 436/518; 436/538; 530/300; 530/350; 530/387.7; 530/388.22; 530/387.9

(58) Field of Classification Search
None
See application file for complete search history.

(56) References Cited

U.S. PATENT DOCUMENTS 7,628,986 B2 * 12/2009 Weber et al.
2009/0220551 A1 * 9/2009 Sampson et al.

FOREIGN PATENT DOCUMENTS

WO    WO 02092771 A2 * 11/2002

OTHER PUBLICATIONS

Safarik et al., Magnetic techniques for the isolation and purification of proteins and peptides, BioMagnetic Res. Technol. 2:7-23, Nov. 26, 2004.*
Komatsu et al., New multiplexed flow cytometric assay to measure anti-peptide antibody: a novel tool for monitoring immune response to peptides used for immunization, Scand. J. Clin. Lab. Invest. 64:535-546, 2004.*
Wade et al., An automated peptide and protein thiazolidine coupling chemistry for biosensor immobilization giving unique N-terminal orientation, Analyt. Biochem. 348:315-317, 2006.*
Heimberger et al., Epidermal growth factor receptor VIII peptide vaccination is efficacious against established intracerebral tumors, Clin. Cancer Res. 9:4247-4254, Sep. 15, 2003.*
Kuan et al., EGF mutant receptor vIII as a molecular target in cancer therapy, Endocrin-related Canc. 8:83-96, 2001.*
Safirik et al., Use of magnetic techniques for the isolation of cells, J. Chromatogr. B. Biomed. Sci. Appl. 722:33-53, 1999.*
Bookman et al., Evaluation of monoclonal humanized anti-HER2 antibody, trastuzumab, in patients with recurrent or refractory ovarian or primary peritoneal carcinoma with overexpression of HER2: A phase II trial of the gynecologic oncology group, J. Clin. Oncol. 21(2): 283-290, Jan. 15, 2003.*
Purev et al.,Immune responses to breast cancer patients to mutated epidermal growth factor receptor (EGF-RvIII, deltaEGF-R, and de2-7 EGF-R), J. Immunol. 173:6472-6480, 2004.*
Purev et al. "Immune response of breast cancer patients to mutated epidermal growth factor receptor (EGF-RvIII, Delta EGF-R, and de2-7 EGF-R)." Journal of Immunology, vol. 173, No. 10, Nov. 15, 2004, pp. 6472-6480.
R.J. Schmittling et al., "Detection of humoral response in patients with glioblastoma receiving EGFRvIII-KLH vaccines." Journal of Immunological Methods Nov. 30, 2008, vol. 339, No. 1, pp. 74-81.
International Search Report for PCT/US2008/070637 dated Nov. 17, 2008.

* cited by examiner

*Primary Examiner* — Claire Kaufman
(74) *Attorney, Agent, or Firm* — Banner & Witcoff, Ltd.

(57) ABSTRACT

Detection of human antibodies directed against the tumor-specific protein Epidermal Growth Factor Receptor variant Class III (EGFRvIII) provide information on tumor burden and vaccine response. The methods of the invention permit the specific identification of antibodies that are able to bind to EGFRvIII. The methods are useful in determining the presence of an EGFRvIII-expressing tumor and in detecting immune responses following immunization with EGFRvIII-derived peptide as part of a cancer immunotherapy regimen.

16 Claims, 4 Drawing Sheets

Example of bead standards (pepIII beads only and FACS PE beads)

Dynabead scatter (FS vs SS)

Fig. 2

EGFRpepIII elution from pep-dynabeads

Results:

|  | eluted beads | eluted supernat assayed | eluted supernat-blocked assayed |
|---|---|---|---|
| PG(normal donor) | 2.64 | 2.33 | 2.3 |
| PG(normal donor) blocked | 2.59 | 2.34 | 2.42 |
| ACT4 | 3.91 | 15.44 | 2.97 |
| ACT4 blocked | 2.01 | 2.44 | 2.45 |
| 81ng/ml L8 in PBS+BSA | 5.41 | 31.2 | 2.57 |
| 81ng/ml L8 in PBS+BSA blocked | 2.16 | 2.21 | 2.11 |

Results indicate that human anti-pepIII was eluted from the Dynabeads(TM) and further demonstrate retention of pepIII activity and specificity based on pepIII blocking.

ASSAY FOR ANTI-EGFRVIII ANTIBODIES

This application claims the benefit of U.S. provisional application 60/950,800 filed Jul. 19, 2007.

FIELD OF THE INVENTION

The invention relates to the field of assays for clinical research, patient monitoring, and drug development purposes.

BACKGROUND OF THE INVENTION

Cancer remains a health issue of global importance. Conventional treatment of cancer has involved surgery, radiation and chemotherapy. However, problems with lack of effectiveness and undesirable side-effects remain and more effective therapies are much sought after for those reasons. The detection of tumor-specific molecules to aid in better diagnosis and treatment of cancer is an area of particularly active research. Tumor-specific molecules offer the possibility of targeted therapy using monoclonal antibodies (mAbs) specifically directed against the tumor-specific molecule. However, it has proven difficult to identify tumor-specific molecules.

Growth factors and their receptors play important roles in regulating cell division, proliferation and migration. One prominent family is the epidermal growth factor receptor (EGFR) family, which consists of four members: EGFR, ErbB-2, ErbB-3 and ErbB-4.

The canonical member of the family, EGFR, is the 170 kilodalton (kDa) membrane glycoprotein of the EGFR gene (c-erbB-1). Overexpression of EGFR in human tumors has been intensively studied, and the EGFR gene has been found amplified and over-expressed in a variety of tumors including malignant human gliomas, such as glioblastoma multiforme (GBM). Other members of the EGFR family, such as ErbB-2 and ErbB-3, have also been shown to have a role in cancer. Indeed, the medical importance of this family is highlighted by the success of trastuzumab (Herceptin), a monoclonal antibody that binds to the ErbB-2 receptor, in treating breast cancer.

Seven genomic variants of the EGF receptor (EGFRv) have been identified to date: class I mutants lack the extracellular domain, resembling the v-erbB gene product; class II mutants contain an in-frame deletion of 83 amino acids in the extracellular domain; class III mutants contain an in-frame deletion with a novel junction amino acid; class IV and V mutants contain deletions in the cytoplasmic domain. Class VI and VII mutants contain Class IV and V mutants co-existing with Class III mutants (See Kuan C T., et al., EGF mutant receptor vIII as a molecular target in cancer therapy. Endocr Relat Cancer. 2001 8:83-96.)

Class III mutants (EGFRvIII) are the most frequently detected genomic variant. 40-50% of GBM tumors have EGFR gene amplification. (EGFRvIII was previously known as a Type II sequence; see, for example, U.S. Pat. No. 5,212, 290). Of those tumors, 50% express the class III deletion. Class III mutants contain a deletion of exons 2-7 of the gene. Removing exons 2-7 causes an in-frame deletion of 801 base pairs of the coding sequence that removes residues 6 to 273 from the extracellular domain of the wild type EGFR protein. Additionally, removal of exons 2-7 results in an inserted glycine residue at position 6 between the residues 5 and 274, near the N-terminus of the extracellular domain. This deletion creates a unique protein sequence and peptides containing the EGFRvIII-unique sequence have been exploited to generate antibodies specific to the EGFRvIII protein. (Wikstrand C J. et al Investigation of a synthetic peptide as immunogen for a variant epidermal growth factor receptor associated with gliomas. 1993 J. Neuroimmunol 46:165-174; Wikstrand C J, et al. Monoclonal antibodies against EGFRvIII are tumor specific and react with breast and lung carcinomas and malignant gliomas. Cancer Res. 1995 55:3140-8; Wikstrand C J, et al. Cell surface localization and density of the tumor-associated variant of the epidermal growth factor receptor, EGFRvIII. Cancer Res. 1997 57:4130-40; Hills D, et al. Specific targeting of a mutant, activated FGF receptor found in glioblastoma using a monoclonal antibody. Int J. Cancer. 1995 63:537-43).

One peptide, known as pepIII, has been used to immunize mice either alone or conjugated to adjuvants such as keyhole limpet haemocyanin (KLH). PepIII is a 13-mer having the sequence LEEKKGNYVVTDH(SEQ ID NO: 2), which contains the inserted glycine residue (underlined). The peptide may be used alone, or coupled to an adjuvant protein, such keyhole limpet haemocyanin (KLH). A cysteine residue can be attached to pepIII to facilitate conjugation to the adjuvant protein. (See Heimberger A B et al. Epidermal growth factor receptor VIII peptide vaccination is efficacious against established intracerebral tumors. Clin Cancer Res. 2003 9: 4247-54.)

Methods for detecting EGFR mutant protein in fluid samples are known in the art; for example, Vogelstein et al. (U.S. Pat. No. 5,212,290) teach the use of a competition based assay. However, direct detection of the protein does not indicate the presence of antibodies directed against EGFRvIII. Detection of mouse antibodies generated against pepIII has been achieved using a standard ELISA assay. (See, for example, U.S. Pat. No. 5,401,828; Heimberger A B et al. supra.) Despite repeated attempts, however, it has not been possible use a standard ELISA assay to detect human anti-EGFRvIII antibodies. Thus, there is a pressing need in the art for an assay that is able to detect human anti-EGFRvIII antibodies reliably.

SUMMARY OF THE INVENTION

In one embodiment of the invention, a method of determining an amount of EGFRvIII-specific antibody in a human blood sample is provided. A first portion of a blood sample is contacted with a peptide, which is immobilized to a solid support. The peptide comprises at least 4 contiguous amino acids of SEQ ID NO: 1, including position 6 of SEQ ID NO: 1. The contacting is performed in the presence of the free form of the peptide. A second portion of the blood sample is contacted with the peptide immobilized to the solid support in the absence of the free form of the peptide. A first amount of antibody is determined from the first portion of the blood sample that bound to the peptide immobilized to the solid support. A second amount of antibody is determined from the second portion of the blood sample that bound to the peptide immobilized to the solid support. A third amount of antibody, which is the amount of antibody specific for EGFRvIII that is present in the human blood sample, is calculated by subtracting the first amount from the second amount.

In an additional embodiment of the invention, a method of determining the presence of a human tumor expressing EGFRvIII is provided. A first portion of a blood sample is contacted with a peptide, which is immobilized to a solid support. The peptide comprises at least 4 contiguous amino acids of SEQ ID NO: 1, including position 6 of SEQ ID NO: 1. The contacting is performed in the presence of the free form of the peptide. A second portion of the blood sample is contacted with the peptide immobilized to the solid support in the absence of the free form of the peptide. A first amount of antibody is determined from the first portion of the blood sample that bound to the peptide immobilized to the solid support. A second amount of antibody is determined from the second portion of the blood sample that bound to the peptide immobilized to the solid support. A third amount of antibody, which is the amount of antibody specific for EGFRvIII that is present in the human blood sample, is calculated by subtracting the first amount from the second amount. The presence of a EGFRvIII-expressing tumor is indicated by the third amount of antibody being above an amount of antibody specific for EGFRvIII determined for a control population of humans who do not have EGFRvIII-expressing tumors.

In an additional embodiment of the invention a method of evaluating a human antibody response to vaccination against EGFRvIII with a peptide is provided. A first portion of a blood sample is contacted with a peptide, which is immobilized to a solid support. The peptide comprises at least 4 contiguous amino acids of SEQ ID NO: 1, including position 6 of SEQ ID NO: 1. The contacting is performed in the presence of the free form of the peptide. A second portion of the blood sample is contacted with the peptide immobilized to the solid support in the absence of the free form of the peptide. A first amount of antibody is determined from the first portion of the blood sample that bound to the peptide immobilized to the solid support. A second amount of antibody is determined from the second portion of the blood sample that bound to the peptide immobilized to the solid support. A third amount of antibody, which is the amount of antibody specific for EGFRvIII that is present in the human blood sample, is calculated by subtracting the first amount from the second amount. An antibody response to vaccination with a peptide against EGFRvIII is indicated by the third amount of antibody being above an amount of antibody specific for EGFRvIII determined for a control population of humans who lack EGFRvIII-expressing tumors and have not been vaccinated against EGFRvIII or if the third amount of antibody is increased over a pre-immunization amount in the human.

In a further embodiment of the invention, a kit is provided. The kit comprises a solid support and a peptide. The peptide comprises at least 4 contiguous amino acids of SEQ ID NO: 1, including position 6 of SEQ ID NO: 1. The kit further comprises free form of an EGFRvIII peptide.

Another embodiment of the invention is a solid support comprising a population of molecules of a peptide immobilized on said solid support. The peptide comprises at least 4 contiguous amino acids of SEQ ID NO: 1 including position 6 of SEQ ID NO: 1.

Still another embodiment of the invention provides a method of evaluating an antibody response to a peptide vaccination against EGFRvIII in a human. A blood sample of the human is contacted with a peptide. The peptide comprises at least 4 contiguous amino acids of SEQ ID NO: 1 including position 6 of SEQ ID NO: 1. An amount of antibody from the blood sample which bound to the peptide is determined. An amount of antibody which is increased over a pre-immunization amount in the human indicates an antibody response to the peptide vaccination in the human.

BRIEF DESCRIPTION OF THE FIGURES

FIG. 2: Elution of anti-pepIII antibody from peptide-conjugated beads. FIG. 2 shows that antibody can be eluted from beads and that the eluted antibody from beads can still bind specifically to pepIII. Six samples are shown: the negative control serum from a normal donor (PG), serum from a patient having anti-pepIII antibody (ACT4), and a positive control (81 ng/ml of L8A4 antibody in PBS+BSA). The remaining three samples are duplicates of the first set of three samples except that free peptide has been added to create "blocked" samples.

DETAILED DESCRIPTION OF THE INVENTION

Figure 1A:
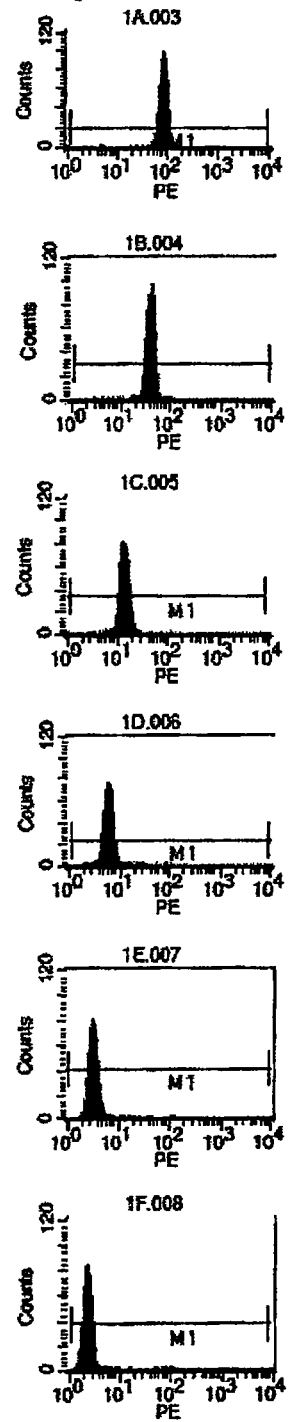
FIG. 1A shows flow cytometry data generated for a standard curve using pepIII-conjugated Dynabeads. Samples A-G contained a range of amounts of the L8A4 anti-pepIII antibody (Sample A contained 81 ng/ml; B, 27 ng/ml; C, 9 ng/ml; D, 3 ng/ml; E, 1 ng/ml; F, 0.33 ng/ml; G, 0.11 ng/ml).

The inventors have found that determining the presence and/or amount of antibodies that are raised in response to an EGFRvIII protein vaccine is a useful indicator of vaccine efficacy. Thus the assaying of antibodies can be used to select peptide vaccines, to guide the modification of peptide vaccines, to guide the formulation of peptide vaccines, to monitor clinical response to peptide vaccines, and to monitor timing of peptide vaccine and booster immunizations. In addition, the presence of antibodies against EGFRvIII protein can be used to infer the presence of an EGFRvIII-expressing tumor. Other applications and uses will be apparent to those of skill in the art.

The inventors have overcome problems inherent in the specific detection of human antibodies able to bind the EGFRvIII protein. By using a subtraction assay, accurate measurements are obtained. Identifying the presence of such antibodies in a clinical sample is useful for both research and medical purposes.

High background levels have hampered the accuracy of direct antibody assays to determine the levels of human antibodies. The inventors have found that high background levels arise due to binding of non-specific antibodies. Non-specific antibodies bind to the peptide-conjugated solid support because of interactions that are not dependent on interactions with the EGFRvIII-derived peptide. These interactions result in a high background level of antibody binding, which can lead to the spurious identification of anti-EGFRvIII antibody in the sample. Such identifications can, for example, lead to undesirable false positive diagnoses of EGFRvIII-expressing tumors or mistaken assessments of an immune response following vaccination with an EGFRvIII-derived peptide.

The inventors have overcome this handicap by determining antibody binding in two samples. The free form of an EGFRvIII peptide is added to the first sample. The first sample provides a measure of non-specific antibody binding only. This sample can be referred to as a "blocked" or "competed" sample. The first sample is prepared by incubating the blood sample with the free form of the peptide before exposing the sample to the solid support. The free form of the peptide contains the same sequence as the peptide immobilized to the solid support. This step allows the free peptide to compete with the solid support-bound peptide. The amount of free peptide to be used in a given assay to saturate the anti-EGFRvIII antibodies in the sample can readily be determined by a skilled artisan.

The second sample contains no free peptide. This sample can be referred to as an "unblocked" or "uncompeted" sample. The second sample provides a measure of both specific and non-specific antibody binding. By subtracting the amount of antibody bound to the solid support in the presence of the free peptide from the amount in the absence, a measure of specific antibody is obtained.

Any biological sample suspected of containing human anti-EGFRvIII antibodies may be used. Typically, blood samples that contain antibody are used, such as whole blood. The blood sample can also be fractions of blood such as serum or plasma can also be used. Often the blood is human blood; however, the blood may be from any animal, including rat, mouse, dog, rabbit, goat, sheep, etc.

The peptides can be immobilized to a variety of suitable solid supports such as the wall of a test tube or nitrocellulose paper. The peptides of the invention may also be immobilized onto wells of multi-well plates. Multi-well plates having different numbers of wells are well known and include 6-well plates, 12-well plates, 24-well plates, 48-well plates, 96-well plates, 384-well plates, 1536-well plates, and the like. The peptides can also be immobilized onto beads. The beads may be made from different materials and can be different sizes. Suitable beads include glass beads, magnetic beads, sepharose beads and latex beads. Typically, magnetic beads can be used. The magnetic beads may be paramagnetic, meaning that beads exhibit magnetic properties in a magnetic field but have little or no residual magnetism once removed from a magnetic field. Suitable paramagnetic beads are available commercially, such as Dynabeads® from Invitrogen (Carlsbad, Calif., U.S.) The beads may also be ferromagnetic, meaning that the beads do not require the presence of an external magnetic field to remain magnetic. The magnetic properties of the beads may be used to isolate the beads from the various solutions used in the assay. Beads known in the art are available in various sizes including from 10-99 nm, 0.1-0.99 µm, and 1-5 µm. Often, beads of 50 nm, 0.8 µm, and 2.8 µm are used. Optionally, an assay may include beads of multiple sizes. Because the beads offer a three dimensional mobile phase to increase binding kinetics, the use of beads provides the opportunity to perform multiparametric analysis within a single sample.

The peptides employed may be any peptide sequence comprising at least 4 contiguous residues of EGFRvIII provided that the sequence contains the glycine residue at position 6 of SEQ ID NO:1 (EGFRvIII protein with mutation). Particular examples include the 13-mer pepIII (LEEKKGNYVVTDH) (SEQ ID NO: 2), the EGFRvIII extracellular domain (ECD) (SEQ ID NO: 3). The full-length EGFRvIII sequence (SEQ ID NO: 1) may be used. Peptides may contain, for example, from 1-1210 amino acid residues, from 4-30, from 5-25, from 6-20, or from 8-15 residues of EGFRvIII. The residues may optionally be fused to additional amino acid residues, such as Cysteine, or Histidine. The peptides may also be fused to all or parts of other proteins to form a fusion protein not found in nature. The peptides may comprise: LEEKKG (SEQ ID NO: 5), EEKKG (SEQ ID NO: 6), EKKG (SEQ ID NO: 7), KKGN (SEQ ID NO: 8), KGNY (SEQ ID NO: 9), GNYV (SEQ ID NO: 10), GNYVV (SEQ ID NO: 11), GNYVVT (SEQ ID NO: 12), GNYVVTD (SEQ ID NO: 13), or GNYVVTDH (SEQ ID NO: 14), as examples. Each of these peptides may be used in soluble or immobilized form in the assay.

The peptides for immobilizing to the support or for use as a free form can be manufactured by any suitable method known in the art. For example, suitable methods include direct synthesis of polypeptides by machine or through molecular biology approaches such as recombinant protein expression. Typically, smaller peptides are synthesized directly. Direct synthesis can also be used to conveniently manufacture other peptides. For example, the number of SEQ ID NO: 1 residues in a peptide can be 4, 5, 6, 7, 8, 9, 10, 11, 12, 13, 14, 15, 16, 17, and so on up to any desired size, such as 1210. With current technology, direct synthesis of peptides becomes inefficient between 70 and 100 residues. While smaller peptides can also be manufactured using a recombinant molecular biology approach, typically this approach is used for larger proteins. Preparation and purification of recombinant proteins by molecular biology is well known in the art. The skilled artisan can readily determine which approach to use for preparing the chosen peptide.

Optionally, additional residues can be added to these peptides to facilitate conjugation of the peptide to the solid support or other substance; for example, a terminal cysteine group may be added to the C-terminus of the peptide.

The peptides may be immobilized to the solid support by any suitable method known in the art. Peptides may be covalently coupled to a solid support having a sulphonyl ester group; for example, according to the manufacturers instructions for Dynabeads® M-280 Tosylactivated, Invitrogen, CA. The support can also have a primary amine group that allows immobilization of the peptide through several different reactions. For example, the peptide may be coupled directly using reductive amination of aldehyde or ketone groups. Alternatively, carbodiimide-activated carboxylic acid groups can be used to immobilize peptide through amide bond formation. Often, the carbodiimide used is 1-ethyl-3-(3-dimethylaminopropyl)carbodiimide hydrochloride (EDC). An amine-reactive cross-linker may also be used with beads having a primary amine group; for example, the cross-linker can be an N-(hydroxy-succinimidyl)-ester (NHS) crosslinker. Carboxylic acid groups of the peptide can also be activated with a carbodiimide and then reacted with the solid support to form an amide bond between the beads and the peptide. Amine-coated beads are available commercially; for example, Dynabeads® M-270 Amine, Invitrogen, CA. A solid support having glycidyl ether (epoxy) groups can also be used to immobilized the peptide. Epoxy-coated beads are commercially available; for example Dynabeads® M-270 Epoxy, Invitrogen, CA. Carboxylic acid coated solid support can be used to form an amide bond between a primary amino group of the peptide by using a carbodiimide or NHS. Optionally, peptides may be immobilized to the solid support by simple adsorption Optionally, the bound and free peptides are different. For example, assays may be performed wherein the bound peptide is the EGFRvIII extracellular domain (ECD) (SEQ ID NO: 3) and the free peptide is the 13-mer pepIII (LEEKKGNYVVTDH) (SEQ ID NO: 2). In a further example, the bound peptide is the 13-mer peptide and the free peptide is the ECD peptide. Other peptides and peptide combinations may be used.

Detection of antibody bound to the immobilized peptide may be performed by any method known in the art. Often, a secondary antibody able to form a complex with the antibody bound to the immobilized peptide i.e., primary antibody, is used. A secondary antibody can be labeled with various detectable moieties such as biotin, peroxidase, alkaline phosphatase, a radiolabel or a fluorescent molecule.

Measurement of the detectable moiety may be by any suitable approach in the art. Measurement of fluorescence intensity may be by any means for detecting a fluorescent signal; for example, flow cytometry or spectrophotometry. Biotin may be detected using avidin, which binds to biotin with high affinity. Typically, the avidin is conjugated to a an enzyme capable of interacting with a chromogenic substrate to generate a measurable signal. Peroxidase and alkaline phosphatase are examples of two such enzymes.

To correlate an amount of signal to an amount of antibody, a standard curve can be created. In one method of creating a standard curve, fluorescence levels are determined for samples containing known amounts of an antibody able to bind EGFRvIII. For example, L8A4 is a monoclonal antibody known to bind to pepIII. (See Wikstrand C J. et al., Cancer Res. 1995 55:3140-8; Reist C J. et al. Tumor-specific antiepidermal growth factor receptor variant III monoclonal antibodies: use of the tyramine-cellobiose radioiodination method enhances cellular retention and uptake in tumor xenografts. Cancer Res. 1995 55:4375-82.) Fluorescence levels corresponding to known amounts of L8A4 antibody can be determined and used to create a standard curve correlating amount of fluorescence to amount of antibody. Fluorescence levels in samples containing unknown amounts of antibody can then be measured. Using the standard curve, the fluorescence level in the unknown sample is correlated to the amount of antibody. Other methods of creating standard curves for the different methods of detection are known in the art.

Figure 1B:
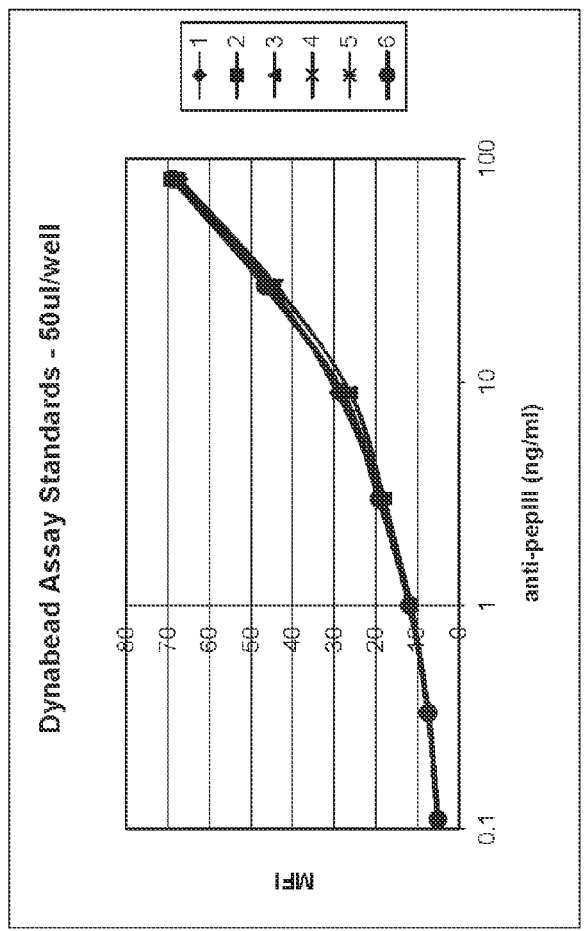
FIG. 1B shows the numerical values and standard curve corresponding to the flow cytometer data shown in FIG. 1. For each amount of antibody, six samples were measured and the average fluorescent score was plotted against the amount of antibody. Samples A-G were the same samples as in FIG. 1A. Sample H contained no antibody.
Figure 1C:
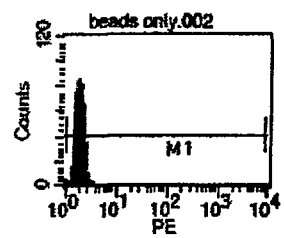
FIG. 1C shows the flow cytometry data for two standards used to calibrate the flow cytometer machine: beads conjugated to pepIII but not exposed to a sample, and beads containing PE, the fluorescent label.
Figure 1C:
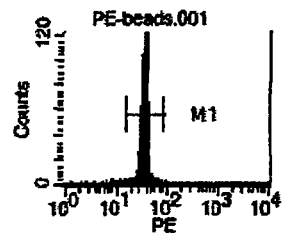
Figure 1C:
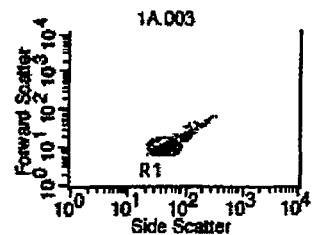

FIGS. 1A, 1B, and 1C show data from a typical standard curve experiment where the fluorescence levels of samples containing the L8A4 antibody were correlated with the amount of antibody added to the samples (81, 27, 9, 1, 0.33, 0.11 ng/ml). The amount of antibody added to the standard curve can be adapted by the artisan to provide an appropriate range for a given assay. A range is appropriate when the amount of antibody in the unknown sample falls between the largest and smallest amounts of antibody added to the samples. By maintaining the amount of antibody in the unknown sample in this range, an accurate measure of the antibody is made.

An additional aspect of the invention is the further study of antibodies that bind to EGFRvIII. Once the antibody is attached to the peptide, the remaining sample can be washed off leaving the antibody bound to the peptide. The isolated anti-EGFRvIII antibodies may be detached from the solid support and further analyzed. For example, the antibodies may be detached from the solid support, concentrated and probed by surface Plasmon resonance or Matrix-assisted laser desorption/ionization time-of-flight mass spectrometer (MALDI-TOF) to determine characteristics of the antibody in one or more samples. Such characteristics include binding affinity and avidity, the structure of the antibody and its amino acid sequence, and the like. For example, further study can also reveal the location on the EGFRvIII peptide where the antibody binds. One approach uses different bound and free peptides. When the free and bound peptides are the same, no antibody attaches to the bound peptide because all antibody attaches to the free peptide. However, in a parallel sample, a different free peptide is used. In that sample, the free peptide can be truncated at either terminus, or have amino acids deleted from an internal region. If antibody binds to the bound peptide in this sample, then the antibody was unable to bind to the free peptide. Such data shows that the antibody binds to the part of the EGFRvIII protein that was removed from the free peptide.

Detachment of the antibody from the peptide may be by any suitable technique. For example using solutions with a pH capable of disrupting antibody-peptide binding can be used. The pH can be acidic; for example, 0.1 M Glycine-HCl, pH 2.3. Alternatively, the pH can be alkaline; for example, 0.1 M Glycine-NaOH, pH 10.0. High salt concentrations can be used; for example, the solution may contain 3.5 M Magnesium chloride, or 3.0 M Potassium chloride, 0.1 M Tris-acetate with 2.0 M NaCl, or 5.0 M Potassium iodide. Detergents can also be used to elute antibody from the immobilized peptide; for example, sodium dodecylsulfate (SDS), or sodium deoxycholate. Solutions containing chaotropic agents can also be used; for example, 2.0 M Urea, 6.0 M Urea, 2.0 M guanidine-HCl, 1.0 M Ammonium thiocyanate. Solutions may contain more than one reagent useful in disrupting the antibody-peptide interaction. Thermal agitation, and organic solvents can also be used. Additionally, incubation of the beads with excess free form of the peptide can also be used to elute antibody from the immobilized peptide.

In yet another aspect of the invention, various components of the invention may be supplied in a package as a kit. The kit may contain the peptide pre-immobilized to the solid support. For example, the peptide may be immobilized to beads or to at least one well of a multi-well plate. Beads of multiple sizes may optionally be included. Rather than supplying peptide pre-immobilized to the solid support, the kit may be supplied with peptide in suitable form for immobilized to a solid support. The peptide may be supplied in dry form, such as a lyophilate. Alternatively, the peptide may be supplied in solution. Optionally, solutions containing peptide can be supplied refrigerated or frozen. The solid support may also be included. Appropriate reagents for immobilization of peptide may also be included. In addition to peptide that is, or can be, immobilized to the solid support, the free form of peptide may be included. The kit may contain one or more reagents for detection of antibody binding. For example, the kit may contain secondary antibodies labeled with any suitable detectable moiety. Optionally, the kit may also contain materials for creating a standard curve. For example, the kit may contain one or more antibodies known to bind to the peptide. One suitable antibody is the L8A4 monoclonal antibody known to bind to pepIII. The various components of the kit may be packaged singly or together. Alternatively, components may be packaged according to storage needs; for example, components that are frozen may be packaged as a discrete group from components that do not require freezing. Optionally, instructions for performing the method of the invention may be included. Immobilized peptides on solid supports can also be supplied and packaged separately, with or without other reagents of the kits described above.

In another aspect of the invention, a modified ELISA may be performed. A modified ELISA employs a multi-well plate as the solid support. Peptide is immobilized to the wells of the multi-well plate. Samples are added to separate wells. The wells are then washed and the amount of antibody bound to the wells is determined. Antibody from the unblocked sample bound to the well provides a measure of total antibody binding. Antibody from the blocked sample bound to the well provides a measure of non-specific antibody binding. The amount of anti-EGFRvIII peptide antibody is determined by subtracting the amount of non-specific antibody binding from the amount of total antibody binding.

All cited references are expressly incorporated herein.

Example 1

Conjugation of PepIII peptide to Magnetic Beads

The PepIII portion of EGFRvIII was covalently linked to magnetic Dynabeads®(Dynal, Invitrogen M-280 Tosylactivated) according to the manufacturer's instructions. Briefly, the beads and PepIII were incubated overnight in borate buffer (pH 9.5) at 37° C. using an end-over-end mixer. The following day the beads were washed with Phosphate Buffered Saline+Bovine Serum Albumin (PBS+BSA) followed by incubation in 0.1M Tris (pH9) to block any remaining active sites on the beads. The beads were adjusted to $2\times10^8$ beads/ml in PBS+0.1% BSA+0.25% Sodium Azide and stored at 2-8° C.

Example 2

Detection of Anti-EGFRvIII Antibodies Using Fluorescently Labeled Anti-Human Secondary Antibody The wells of a polystyrene flat bottom 96 well plate were prepared by adding 200 µl of a PBS+1% BSA solution to each well and incubating the plate for 30 minutes at 37° C. After this incubation, the solution was decanted and excess liquid was blotted.

Three types of sample were added to the plate: serum from a patient known to contain anti-pepIII antibody, serum from a patient known to have no antibody, and a third sample set containing defined amounts of a known anti-pepIII antibody. The third sample set was used to create a standard curve, which allows correlation of the amount of fluorescence to a known amount of antibody.

Samples from patient serum were diluted 1:10 with PBS+ 1% BSA before use. 50 µl of each sample was added into the wells. To determine the specificity of anti-pepIII antibody binding, 450 ng (20 µl of a 25 µg/ml solution) of free pepIII peptide was added to an additional sample set to create the "blocked" sample. The free peptide binds to any anti-pepIII antibody present in the serum preventing the anti-pepIII antibodies from binding to the pepIII conjugated to the beads. Samples pre-incubated with the peptide are shown in the figures as "blocked" samples. To maintain the correct volume in the wells, 20 µl of PBS+1% BSA was added to the other samples.

The plate was incubated on a mixer for 10 minutes at room temperature to allow any antibody present in the samples to bind to the added free peptide. After the minute incubation, approximately $3\times10^5$ pepIII-conjugated beads were added to the wells. The beads were diluted in PBS+0.2% Tween 20 such that the $3\times10^5$ beads were contained in 20 µl.

The beads and sample were mixed on a vortex mixer for 30 minutes at room temperature. After the 30 minute incubation, the breads were washed twice with Wash Buffer (PBS+0.1% Tween 20). For each washing step, a magnetic plate holder was used to retain the beads. Recapture of the beads following each addition of Wash Buffer required at least 30 seconds.

Following the washing steps, the beads were incubated in the dark for 30 minutes with the secondary antibody GAH-PE (goat anti-human phycoerythrin). After the second 30 minute incubation, the beads were washed twice with Wash Buffer to remove excess secondary antibody. Finally, 100 µl of Wash Buffer was added to each well and the beads were resuspended by mixing and transferred to FACS tubes containing an additional 100 µl of Wash Buffer. The fluorescent signal was analyzed on a flow cytometer. Typical data are shown in FIGS. 1A and 1B, which present flow cytometry data and corresponding numerical values, respectively, for assays performed using the L8A4 antibody.

Using this approach, antibody detection was about 0.3 ng (1.8 µM). Sensitivity may be improved further, however, by using immunoassay amplification methods known in the art.

Example 3

Elution of Anti-EGFRvIII Antibody from Beads

Anti-pepIII antibodies were bound from samples, essentially as described above, in 50 µl samples in a 96-well plate. Each well also contained 20 µl of pepIII-conjugated-dynabeads The beads with bound antibody were washed for 30 minutes on a mixer in the PBS+0.1% Tween 20. 100 µl of elution buffer was added and the beads were incubated for 30 seconds. After 30 seconds, 13 µl of neutralization buffer was added. The beads were re-isolated and rinsed with Wash Buffer. Both the beads and the eluted supernatant were retained.

The eluted supernatant from each of six samples were analyzed to measure the presence of anti-pepIII antibody by a second round of binding to pepIII-conjugated beads in the presence and absence of free peptide.

FIG. 2 shows the results obtained by following this method. PG serum sample was taken from a normal donor who did not have antibodies to EGFRvIII for use as a negative control. ACT4 is from a patient known to have an EGFRvIII tumor and antibodies thereto. The third sample, L8A4, contains PBS+0.5% BSA to which was added 81 ng/ml of the L8A4 anti-pepIII antibody for use as a positive control. Samples incubated with free peptide in the first round of binding are identified as "blocked" samples. Testing of the eluted supernatant shows that no antibody was detected in "blocked" samples. (See middle column of FIG. 2; PG blocked=2.34; ACT block=2.44; L8A4=2.21).

In the unblocked sample from the normal donor negative control (PG), no antibody was detected. Antibody levels for the PG sample eluted supernatant sample was 2.33. Because the blocked sample antibody levels were 2.34, the only binding detected was non-specific binding.

In contrast, anti-pepIII antibody was detected in the eluted supernatants from both the ACT4 serum (15.44) and the positive control sample spiked with the L8A4 antibody (31.2). Thus, in both those samples, anti-pepIII antibody bound to the beads and then was eluted from the beads successfully.

The data in FIG. 2 further show that the eluted antibodies in the supernatant both retained binding activity and were able to bind the pepIII peptide specifically. When the eluted supernatant was mixed with beads and free peptide, the amount of antibody bound was reduced to background levels (ACT4=2.97; L8A4=2.57). The absence of antibody from the beads is due to eluted antibody binding the pepIII peptide and remaining in the supernatant.

Elution of antibody from the beads was effective as only a small amount of antibody remained bound to the beads after the treatment.

The invention claimed is:

1. A method of determining an amount of EGFRvIII-specific antibody in a blood sample of a human, comprising:
   contacting a first portion of the blood sample with a peptide immobilized to a solid support, wherein the peptide comprises at least 4 and up to 17 contiguous amino acids of SEQ ID NO: 1 including position 6 of SEQ ID NO: 1; wherein the contacting is performed in the presence of a free form of the peptide of at least 4 and up to 17 contiguous amino acids of SEQ ID NO: 1;
   contacting a second portion of the blood sample with the peptide immobilized to the solid support, wherein the contacting is performed in the absence of the free form of the peptide;
   determining a first amount of antibody from the first portion of the blood sample which bound to the peptide immobilized to the solid support;
   determining a second amount of antibody from the second portion of the blood sample which bound to the peptide immobilized to the solid support;
   calculating a third amount by subtracting the first amount from the second amount, said third amount representing EGFRvIII-specific antibody in the blood sample of the human.

2. A method of determining presence of an EGFRvIII expressing tumor in a human who has not been vaccinated against EGFRvIII, comprising the steps of:
   contacting a first portion of a blood sample from the human with a peptide immobilized to a solid support, wherein the peptide comprises at least 4 and up to 17 contiguous amino acids of SEQ ID NO: 1 including position 6 of SEQ ID NO: 1; wherein the contacting is performed in the presence of a free form of the peptide of at least 4 and up to 17 contiguous amino acids of SEQ ID NO: 1;
   contacting a second portion of the blood sample from the human with the peptide immobilized to the solid support, wherein the contacting is performed in the absence of the free form of the peptide;
   determining a first amount of antibody from the first portion of the blood sample which bound to the peptide immobilized to the solid support;
   determining a second amount of antibody from the second portion of the blood sample which bound to the peptide immobilized to the solid support;
   calculating a third amount by subtracting the first amount from the second amount, said third amount representing EGFRvIII-specific antibody in the blood sample of the human, wherein a third amount of antibody which is above amounts determined for a population of control humans who do not have EGFRvIII expressing tumors and who have not been vaccinated against EGFRvIII indicates presence of an EGFRvIII expressing tumor in the human.

3. A method of evaluating an antibody response to a peptide vaccination against EGFRvIII in a human, comprising the steps of:
   contacting a first portion of a blood sample of the human obtained after the peptide vaccination with a peptide immobilized to a solid support, wherein the peptide comprises at least 4 and up to 17 contiguous amino acids of SEQ ID NO: 1 including position 6 of SEQ ID NO: 1; wherein the contacting is performed in the presence of a free form of the peptide of at least 4 and up to 17 contiguous amino acids of SEQ ID NO: 1;
   contacting a second portion of the blood sample with the peptide immobilized to the solid support, wherein the contacting is performed in the absence of the free form of the peptide;
   determining a first amount of antibody from the first portion of the blood sample which bound to the peptide immobilized to the solid support;
   determining a second amount of antibody from the second portion of the blood sample which bound to the peptide immobilized to the solid support;
   calculating a third amount by subtracting the first amount from the second amount, said third amount representing EGFRvIII-specific antibody in the blood sample of the human, wherein a third amount of antibody which is above amounts determined for a population of control humans who do not have EGFRvIII expressing tumors and who have not been vaccinated against EGFRvIII or a third amount of antibody which is increased over a pre-immunization amount in the human indicates an antibody response to the peptide vaccination in the human.

4. The method of claim 1, 2, or 3 wherein the human has previously had an EGFRvIII expressing tumor which had been removed or treated.

5. The method of claim 1, 2, or 3 wherein the solid support is a bead.

6. The method of claim 1, 2, or 3 wherein the solid support is a well of a multi-well plate.

7. The method of claim 1, 2, or 3 wherein the solid support is a magnetic bead.

8. The method of claim 1, 2, or 3 wherein the solid support is a ferromagnetic bead.

9. The method of claim 1, 2, or 3 wherein the solid support is a paramagnetic bead.

10. The method of claim 1, 2, or 3 wherein the steps of determining a first and second amount of antibody bound to the peptide employ a second antibody which binds to human antibodies.

11. The method of claim 1, 2, or 3 wherein the solid support comprises a population of beads of multiple sizes.

12. The method of claim 4 wherein flow cytometry is used to measure the fluorescence intensity of the beads.

13. The method of claim 1, 2, or 3 wherein the blood sample is a blood fraction.

14. The method of claim 1, wherein the free form of the peptide is contacted with the first portion of the blood sample prior to contacting of the first portion of the blood sample with the peptide immobilized to a solid support.

15. The method of claim 2 wherein the free form of the peptide is contacted with the first portion of the blood sample prior to contacting of the first portion of the blood sample with the peptide immobilized to a solid support.

16. The method of claim 3 wherein the free form of the peptide is contacted with the first portion of the blood sample prior to contacting of the first portion of the blood sample with the peptide immobilized to a solid support.

* * * * *

SEQUENCE LISTING

```
<160> NUMBER OF SEQ ID NOS: 15

<210> SEQ ID NO 1
<211> LENGTH: 919
<212> TYPE: PRT
<213> ORGANISM: Homo sapiens
```

-continued

<400> SEQUENCE: 1

| | | | | | | | | | | | | | | |
|---|---|---|---|---|---|---|---|---|---|---|---|---|---|---|
| Leu | Glu | Glu | Lys | Lys | Gly | Asn | Tyr | Val | Thr | Asp | His | Gly | Ser | Cys |
| 1 | | | | 5 | | | | | 10 | | | | | 15 |
| Val | Arg | Ala | Cys | Gly | Ala | Asp | Ser | Tyr | Glu | Met | Glu | Glu | Asp | Gly | Val |
| | | | 20 | | | | | 25 | | | | | 30 | | |
| Arg | Lys | Cys | Lys | Lys | Cys | Glu | Gly | Pro | Cys | Arg | Lys | Val | Cys | Asn | Gly |
| | | 35 | | | | | 40 | | | | | 45 | | | |
| Ile | Gly | Ile | Gly | Glu | Phe | Lys | Asp | Ser | Leu | Ser | Ile | Asn | Ala | Thr | Asn |
| | 50 | | | | | 55 | | | | | 60 | | | | |
| Ile | Lys | His | Phe | Lys | Asn | Cys | Thr | Ser | Ile | Ser | Gly | Asp | Leu | His | Ile |
| 65 | | | | | 70 | | | | | 75 | | | | | 80 |
| Leu | Pro | Val | Ala | Phe | Arg | Gly | Asp | Ser | Phe | Thr | His | Thr | Pro | Pro | Leu |
| | | | | 85 | | | | | 90 | | | | | 95 | |
| Asp | Pro | Gln | Glu | Leu | Asp | Ile | Leu | Lys | Thr | Val | Lys | Glu | Ile | Thr | Gly |
| | | | 100 | | | | | 105 | | | | | 110 | | |
| Phe | Leu | Leu | Ile | Gln | Ala | Trp | Pro | Glu | Asn | Arg | Thr | Asp | Leu | His | Ala |
| | | 115 | | | | | 120 | | | | | 125 | | | |
| Phe | Glu | Asn | Leu | Glu | Ile | Ile | Arg | Gly | Arg | Thr | Lys | Gln | His | Gly | Gln |
| | 130 | | | | | 135 | | | | | 140 | | | | |
| Phe | Ser | Leu | Ala | Val | Val | Ser | Leu | Asn | Ile | Thr | Ser | Leu | Gly | Leu | Arg |
| 145 | | | | | 150 | | | | | 155 | | | | | 160 |
| Ser | Leu | Lys | Glu | Ile | Ser | Asp | Gly | Asp | Val | Ile | Ile | Ser | Gly | Asn | Lys |
| | | | | 165 | | | | | 170 | | | | | 175 | |
| Asn | Leu | Cys | Tyr | Ala | Asn | Thr | Ile | Asn | Trp | Lys | Lys | Leu | Phe | Gly | Thr |
| | | | 180 | | | | | 185 | | | | | 190 | | |
| Ser | Gly | Gln | Lys | Thr | Lys | Ile | Ile | Ser | Asn | Arg | Gly | Glu | Asn | Ser | Cys |
| | | 195 | | | | | 200 | | | | | 205 | | | |
| Lys | Ala | Thr | Gly | Gln | Val | Cys | His | Ala | Leu | Cys | Ser | Pro | Glu | Gly | Cys |
| | 210 | | | | | 215 | | | | | 220 | | | | |
| Trp | Gly | Pro | Glu | Pro | Arg | Asp | Cys | Val | Ser | Cys | Arg | Asn | Val | Ser | Arg |
| 225 | | | | | 230 | | | | | 235 | | | | | 240 |
| Gly | Arg | Glu | Cys | Val | Asp | Lys | Cys | Asn | Leu | Leu | Glu | Gly | Glu | Pro | Arg |
| | | | | 245 | | | | | 250 | | | | | 255 | |
| Glu | Phe | Val | Glu | Asn | Ser | Glu | Cys | Ile | Gln | Cys | His | Pro | Glu | Cys | Leu |
| | | | 260 | | | | | 265 | | | | | 270 | | |
| Pro | Gln | Ala | Met | Asn | Ile | Thr | Cys | Thr | Gly | Arg | Gly | Pro | Asp | Asn | Cys |
| | | 275 | | | | | 280 | | | | | 285 | | | |
| Ile | Gln | Cys | Ala | His | Tyr | Ile | Asp | Gly | Pro | His | Cys | Val | Lys | Thr | Cys |
| | 290 | | | | | 295 | | | | | 300 | | | | |
| Pro | Ala | Gly | Val | Met | Gly | Glu | Asn | Asn | Thr | Leu | Val | Trp | Lys | Tyr | Ala |
| 305 | | | | | 310 | | | | | 315 | | | | | 320 |
| Asp | Ala | Gly | His | Val | Cys | His | Leu | Cys | His | Pro | Asn | Cys | Thr | Tyr | Gly |
| | | | | 325 | | | | | 330 | | | | | 335 | |
| Cys | Thr | Gly | Pro | Gly | Leu | Glu | Gly | Cys | Pro | Thr | Asn | Gly | Pro | Lys | Ile |
| | | | 340 | | | | | 345 | | | | | 350 | | |
| Pro | Ser | Ile | Ala | Thr | Gly | Met | Val | Gly | Ala | Leu | Leu | Leu | Leu | Leu | Val |
| | | 355 | | | | | 360 | | | | | 365 | | | |
| Val | Ala | Leu | Gly | Ile | Gly | Leu | Phe | Met | Arg | Arg | Arg | His | Ile | Val | Arg |
| | 370 | | | | | 375 | | | | | 380 | | | | |
| Lys | Arg | Thr | Leu | Arg | Arg | Leu | Leu | Gln | Glu | Arg | Glu | Leu | Val | Glu | Pro |
| 385 | | | | | 390 | | | | | 395 | | | | | 400 |
| Leu | Thr | Pro | Ser | Gly | Glu | Ala | Pro | Asn | Gln | Ala | Leu | Leu | Arg | Ile | Leu |
| | | | | 405 | | | | | 410 | | | | | 415 | |

```
Lys Glu Thr Glu Phe Lys Lys Ile Lys Val Leu Gly Ser Gly Ala Phe
                420                 425                 430
Gly Thr Val Tyr Lys Gly Leu Trp Ile Pro Glu Gly Glu Lys Val Lys
            435                 440                 445
Ile Pro Val Ala Ile Lys Glu Leu Arg Glu Ala Thr Ser Pro Lys Ala
450                 455                 460
Asn Lys Glu Ile Leu Asp Glu Ala Tyr Val Met Ala Ser Val Asp Asn
465                 470                 475                 480
Pro His Val Cys Arg Leu Leu Gly Ile Cys Leu Thr Ser Thr Val Gln
                485                 490                 495
Leu Ile Thr Gln Leu Met Pro Phe Gly Cys Leu Leu Asp Tyr Val Arg
            500                 505                 510
Glu His Lys Asp Asn Ile Gly Ser Gln Tyr Leu Leu Asn Trp Cys Val
        515                 520                 525
Gln Ile Ala Lys Gly Met Asn Tyr Leu Glu Asp Arg Arg Leu Val His
    530                 535                 540
Arg Asp Leu Ala Ala Arg Asn Val Leu Val Lys Thr Pro Gln His Val
545                 550                 555                 560
Lys Ile Thr Asp Phe Gly Leu Ala Lys Leu Leu Gly Ala Glu Glu Lys
                565                 570                 575
Glu Tyr His Ala Glu Gly Gly Lys Val Pro Ile Lys Trp Met Ala Leu
            580                 585                 590
Glu Ser Ile Leu His Arg Ile Tyr Thr His Gln Ser Asp Val Trp Ser
        595                 600                 605
Tyr Gly Val Thr Val Trp Glu Leu Met Thr Phe Gly Ser Lys Pro Tyr
    610                 615                 620
Asp Gly Ile Pro Ala Ser Glu Ile Ser Ser Ile Leu Glu Lys Gly Glu
625                 630                 635                 640
Arg Leu Pro Gln Pro Pro Ile Cys Thr Ile Asp Val Tyr Met Ile Met
                645                 650                 655
Val Lys Cys Trp Met Ile Asp Ala Asp Ser Arg Pro Lys Phe Arg Glu
            660                 665                 670
Leu Ile Ile Glu Phe Ser Lys Met Ala Arg Asp Pro Gln Arg Tyr Leu
        675                 680                 685
Val Ile Gln Gly Asp Glu Arg Met His Leu Pro Ser Pro Thr Asp Ser
    690                 695                 700
Asn Phe Tyr Arg Ala Leu Met Asp Glu Glu Asp Met Asp Asp Val Val
705                 710                 715                 720
Asp Ala Asp Glu Tyr Leu Ile Pro Gln Gln Gly Phe Phe Ser Ser Pro
                725                 730                 735
Ser Thr Ser Arg Thr Pro Leu Leu Ser Ser Leu Ser Ala Thr Ser Asn
            740                 745                 750
Asn Ser Thr Val Ala Cys Ile Asp Arg Asn Gly Leu Gln Ser Cys Pro
        755                 760                 765
Ile Lys Glu Asp Ser Phe Leu Gln Arg Tyr Ser Ser Asp Pro Thr Gly
    770                 775                 780
Ala Leu Thr Glu Asp Ser Ile Asp Asp Thr Phe Leu Pro Val Pro Glu
785                 790                 795                 800
Tyr Ile Asn Gln Ser Val Pro Lys Arg Pro Ala Gly Ser Val Gln Asn
                805                 810                 815
Pro Val Tyr His Asn Gln Pro Leu Asn Pro Ala Pro Ser Arg Asp Pro
            820                 825                 830
```

```
His Tyr Gln Asp Pro His Ser Thr Ala Val Gly Asn Pro Glu Tyr Leu
            835                 840                 845
Asn Thr Val Gln Pro Thr Cys Val Asn Ser Thr Phe Asp Ser Pro Ala
850                 855                 860
His Trp Ala Gln Lys Gly Ser His Gln Ile Ser Leu Asp Asn Pro Asp
865                 870                 875                 880
Tyr Gln Gln Asp Phe Phe Pro Lys Glu Ala Lys Pro Asn Gly Ile Phe
            885                 890                 895
Lys Gly Ser Thr Ala Glu Asn Ala Glu Tyr Leu Arg Val Ala Pro Gln
            900                 905                 910
Ser Ser Glu Phe Ile Gly Ala
            915

<210> SEQ ID NO 2
<211> LENGTH: 13
<212> TYPE: PRT
<213> ORGANISM: Homo sapiens

<400> SEQUENCE: 2

Leu Glu Glu Lys Lys Gly Asn Tyr Val Val Thr Asp His
1               5                   10

<210> SEQ ID NO 3
<211> LENGTH: 354
<212> TYPE: PRT
<213> ORGANISM: Homo sapiens

<400> SEQUENCE: 3

Leu Glu Glu Lys Lys Gly Asn Tyr Val Val Thr Asp His Gly Ser Cys
1               5                   10                  15
Val Arg Ala Cys Gly Ala Asp Ser Tyr Glu Met Glu Glu Asp Gly Val
            20                  25                  30
Arg Lys Cys Lys Lys Cys Glu Gly Pro Cys Arg Lys Val Cys Asn Gly
        35                  40                  45
Ile Gly Ile Gly Glu Phe Lys Asp Ser Leu Ser Ile Asn Ala Thr Asn
    50                  55                  60
Ile Lys His Phe Lys Asn Cys Thr Ser Ile Ser Gly Asp Leu His Ile
65                  70                  75                  80
Leu Pro Val Ala Phe Arg Gly Asp Ser Phe Thr His Thr Pro Pro Leu
                85                  90                  95
Asp Pro Gln Glu Leu Asp Ile Leu Lys Thr Val Lys Glu Ile Thr Gly
            100                 105                 110
Phe Leu Leu Ile Gln Ala Trp Pro Glu Asn Arg Thr Asp Leu His Ala
        115                 120                 125
Phe Glu Asn Leu Glu Ile Ile Arg Gly Arg Thr Lys Gln His Gly Gln
    130                 135                 140
Phe Ser Leu Ala Val Val Ser Leu Asn Ile Thr Ser Leu Gly Leu Arg
145                 150                 155                 160
Ser Leu Lys Glu Ile Ser Asp Gly Asp Val Ile Ile Ser Gly Asn Lys
                165                 170                 175
Asn Leu Cys Tyr Ala Asn Thr Ile Asn Trp Lys Lys Leu Phe Gly Thr
            180                 185                 190
Ser Gly Gln Lys Thr Lys Ile Ile Ser Asn Arg Gly Glu Asn Ser Cys
        195                 200                 205
Lys Ala Thr Gly Gln Val Cys His Ala Leu Cys Ser Pro Glu Gly Cys
    210                 215                 220
```

```
Trp Gly Pro Glu Pro Arg Asp Cys Val Ser Cys Arg Asn Val Ser Arg
225                 230                 235                 240

Gly Arg Glu Cys Val Asp Lys Cys Asn Leu Leu Glu Gly Glu Pro Arg
            245                 250                 255

Glu Phe Val Glu Asn Ser Glu Cys Ile Gln Cys His Pro Glu Cys Leu
        260                 265                 270

Pro Gln Ala Met Asn Ile Thr Cys Thr Gly Arg Gly Pro Asp Asn Cys
    275                 280                 285

Ile Gln Cys Ala His Tyr Ile Asp Gly Pro His Cys Val Lys Thr Cys
290                 295                 300

Pro Ala Gly Val Met Gly Glu Asn Asn Thr Leu Val Trp Lys Tyr Ala
305                 310                 315                 320

Asp Ala Gly His Val Cys His Leu Cys His Pro Asn Cys Thr Tyr Gly
                325                 330                 335

Cys Thr Gly Pro Gly Leu Glu Gly Cys Pro Thr Asn Gly Pro Lys Ile
            340                 345                 350

Pro Ser

<210> SEQ ID NO 4
<211> LENGTH: 1210
<212> TYPE: PRT
<213> ORGANISM: Homo sapiens

<400> SEQUENCE: 4

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240
```

```
-continued

Thr Gly Pro Arg Glu Ser Asp Cys Leu Val Cys Arg Lys Phe Arg Asp
                245                 250                 255
Glu Ala Thr Cys Lys Asp Thr Cys Pro Pro Leu Met Leu Tyr Asn Pro
            260                 265                 270
Thr Thr Tyr Gln Met Asp Val Asn Pro Glu Gly Lys Tyr Ser Phe Gly
        275                 280                 285
Ala Thr Cys Val Lys Lys Cys Pro Arg Asn Tyr Val Val Thr Asp His
290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                325                 330                 335
Cys Asn Gly Ile Gly Ile Gly Glu Phe Lys Asp Ser Leu Ser Ile Asn
            340                 345                 350
Ala Thr Asn Ile Lys His Phe Lys Asn Cys Thr Ser Ile Ser Gly Asp
        355                 360                 365
Leu His Ile Leu Pro Val Ala Phe Arg Gly Asp Ser Phe Thr His Thr
370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
        435                 440                 445
Gly Leu Arg Ser Leu Lys Glu Ile Ser Asp Gly Asp Val Ile Ile Ser
450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
        515                 520                 525
Val Ser Arg Gly Arg Glu Cys Val Asp Lys Cys Asn Leu Leu Glu Gly
530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
        595                 600                 605
Lys Tyr Ala Asp Ala Gly His Val Cys His Leu Cys His Pro Asn Cys
610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
```

-continued

```
                660                 665                 670
Ile Val Arg Lys Arg Thr Leu Arg Arg Leu Leu Gln Glu Arg Glu Leu
            675                 680                 685

Val Glu Pro Leu Thr Pro Ser Gly Glu Ala Pro Asn Gln Ala Leu Leu
690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe Phe
    1010                1015                1020

Ser Ser Pro Ser Thr Ser Arg Thr Pro Leu Leu Ser Ser Leu Ser Ala
1025                1030                1035                1040

Thr Ser Asn Asn Ser Thr Val Ala Cys Ile Asp Arg Asn Gly Leu Gln
                1045                1050                1055

Ser Cys Pro Ile Lys Glu Asp Ser Phe Leu Gln Arg Tyr Ser Ser Asp
            1060                1065                1070

Pro Thr Gly Ala Leu Thr Glu Asp Ser Ile Asp Asp Thr Phe Leu Pro
        1075                1080                1085
```

-continued

Val Pro Glu Tyr Ile Asn Gln Ser Val Pro Lys Arg Pro Ala Gly Ser
    1090                1095                1100

Val Gln Asn Pro Val Tyr His Asn Gln Pro Leu Asn Pro Ala Pro Ser
1105                1110                1115                1120

Arg Asp Pro His Tyr Gln Asp Pro His Ser Thr Ala Val Gly Asn Pro
                1125                1130                1135

Glu Tyr Leu Asn Thr Val Gln Pro Thr Cys Val Asn Ser Thr Phe Asp
                1140                1145                1150

Ser Pro Ala His Trp Ala Gln Lys Gly Ser His Gln Ile Ser Leu Asp
            1155                1160                1165

Asn Pro Asp Tyr Gln Gln Asp Phe Phe Pro Lys Glu Ala Lys Pro Asn
        1170                1175                1180

Gly Ile Phe Lys Gly Ser Thr Ala Glu Asn Ala Glu Tyr Leu Arg Val
1185                1190                1195                1200

Ala Pro Gln Ser Ser Glu Phe Ile Gly Ala
                1205                1210

<210> SEQ ID NO 5
<211> LENGTH: 6
<212> TYPE: PRT
<213> ORGANISM: Homo sapiens

<400> SEQUENCE: 5

Leu Glu Glu Lys Lys Gly
1               5

<210> SEQ ID NO 6
<211> LENGTH: 5
<212> TYPE: PRT
<213> ORGANISM: Homo sapiens

<400> SEQUENCE: 6

Glu Glu Lys Lys Gly
1               5

<210> SEQ ID NO 7
<211> LENGTH: 4
<212> TYPE: PRT
<213> ORGANISM: Homo sapiens

<400> SEQUENCE: 7

Glu Lys Lys Gly
1

<210> SEQ ID NO 8
<211> LENGTH: 4
<212> TYPE: PRT
<213> ORGANISM: Homo sapiens

<400> SEQUENCE: 8

Lys Lys Gly Asn
1

<210> SEQ ID NO 9
<211> LENGTH: 4
<212> TYPE: PRT
<213> ORGANISM: Homo sapiens

<400> SEQUENCE: 9

Lys Gly Asn Tyr
1

```
<210> SEQ ID NO 10
<211> LENGTH: 4
<212> TYPE: PRT
<213> ORGANISM: Homo sapiens

<400> SEQUENCE: 10

Gly Asn Tyr Val
 1

<210> SEQ ID NO 11
<211> LENGTH: 5
<212> TYPE: PRT
<213> ORGANISM: Homo sapiens

<400> SEQUENCE: 11

Gly Asn Tyr Val Val
 1               5

<210> SEQ ID NO 12
<211> LENGTH: 6
<212> TYPE: PRT
<213> ORGANISM: Homo sapiens

<400> SEQUENCE: 12

Gly Asn Tyr Val Val Thr
 1               5

<210> SEQ ID NO 13
<211> LENGTH: 7
<212> TYPE: PRT
<213> ORGANISM: Homo sapiens

<400> SEQUENCE: 13

Gly Asn Tyr Val Val Thr Asp
 1               5

<210> SEQ ID NO 14
<211> LENGTH: 8
<212> TYPE: PRT
<213> ORGANISM: Homo sapiens

<400> SEQUENCE: 14

Gly Asn Tyr Val Val Thr Asp His
 1               5

<210> SEQ ID NO 15
<211> LENGTH: 943
<212> TYPE: PRT
<213> ORGANISM: Homo sapiens

<400> SEQUENCE: 15

Met Arg Pro Ser Gly Thr Ala Gly Ala Ala Leu Leu Ala Leu Leu Ala
 1               5                  10                  15

Ala Leu Cys Pro Ala Ser Arg Ala Leu Glu Glu Lys Lys Gly Asn Tyr
                20                  25                  30

Val Val Thr Asp His Gly Ser Cys Val Arg Ala Cys Gly Ala Asp Ser
                35                  40                  45

Tyr Glu Met Glu Glu Asp Gly Val Arg Lys Cys Lys Lys Cys Glu Gly
                50                  55                  60

Pro Cys Arg Lys Val Cys Asn Gly Ile Gly Ile Gly Glu Phe Lys Asp
65                  70                  75                  80
```

```
Ser Leu Ser Ile Asn Ala Thr Asn Ile Lys His Phe Lys Asn Cys Thr
                 85                  90                  95
Ser Ile Ser Gly Asp Leu His Ile Leu Pro Val Ala Phe Arg Gly Asp
            100                 105                 110
Ser Phe Thr His Thr Pro Pro Leu Asp Pro Gln Glu Leu Asp Ile Leu
            115                 120                 125
Lys Thr Val Lys Glu Ile Thr Gly Phe Leu Leu Ile Gln Ala Trp Pro
130                 135                 140
Glu Asn Arg Thr Asp Leu His Ala Phe Glu Asn Leu Glu Ile Ile Arg
145                 150                 155                 160
Gly Arg Thr Lys Gln His Gly Gln Phe Ser Leu Ala Val Val Ser Leu
                165                 170                 175
Asn Ile Thr Ser Leu Gly Leu Arg Ser Leu Lys Glu Ile Ser Asp Gly
            180                 185                 190
Asp Val Ile Ile Ser Gly Asn Lys Asn Leu Cys Tyr Ala Asn Thr Ile
            195                 200                 205
Asn Trp Lys Lys Leu Phe Gly Thr Ser Gly Gln Lys Thr Lys Ile Ile
210                 215                 220
Ser Asn Arg Gly Glu Asn Ser Cys Lys Ala Thr Gly Gln Val Cys His
225                 230                 235                 240
Ala Leu Cys Ser Pro Glu Gly Cys Trp Gly Pro Glu Pro Arg Asp Cys
                245                 250                 255
Val Ser Cys Arg Asn Val Ser Arg Gly Arg Glu Cys Val Asp Lys Cys
            260                 265                 270
Asn Leu Leu Glu Gly Glu Pro Arg Glu Phe Val Glu Asn Ser Glu Cys
            275                 280                 285
Ile Gln Cys His Pro Glu Cys Leu Pro Gln Ala Met Asn Ile Thr Cys
290                 295                 300
Thr Gly Arg Gly Pro Asp Asn Cys Ile Gln Cys Ala His Tyr Ile Asp
305                 310                 315                 320
Gly Pro His Cys Val Lys Thr Cys Pro Ala Gly Val Met Gly Glu Asn
                325                 330                 335
Asn Thr Leu Val Trp Lys Tyr Ala Asp Ala Gly His Val Cys His Leu
            340                 345                 350
Cys His Pro Asn Cys Thr Tyr Gly Cys Thr Gly Pro Gly Leu Glu Gly
            355                 360                 365
Cys Pro Thr Asn Gly Pro Lys Ile Pro Ser Ile Ala Thr Gly Met Val
370                 375                 380
Gly Ala Leu Leu Leu Leu Leu Val Val Ala Leu Gly Ile Gly Leu Phe
385                 390                 395                 400
Met Arg Arg Arg His Ile Val Arg Lys Arg Thr Leu Arg Arg Leu Leu
                405                 410                 415
Gln Glu Arg Glu Leu Val Glu Pro Leu Thr Pro Ser Gly Glu Ala Pro
            420                 425                 430
Asn Gln Ala Leu Leu Arg Ile Leu Lys Glu Thr Glu Phe Lys Lys Ile
            435                 440                 445
Lys Val Leu Gly Ser Gly Ala Phe Gly Thr Val Tyr Lys Gly Leu Trp
450                 455                 460
Ile Pro Glu Gly Glu Lys Val Lys Ile Pro Val Ala Ile Lys Glu Leu
465                 470                 475                 480
Arg Glu Ala Thr Ser Pro Lys Ala Asn Lys Glu Ile Leu Asp Glu Ala
                485                 490                 495
Tyr Val Met Ala Ser Val Asp Asn Pro His Val Cys Arg Leu Leu Gly
```

```
            500                 505                 510
Ile Cys Leu Thr Ser Thr Val Gln Leu Ile Thr Gln Leu Met Pro Phe
            515                 520                 525
Gly Cys Leu Leu Asp Tyr Val Arg Glu His Lys Asp Asn Ile Gly Ser
            530                 535                 540
Gln Tyr Leu Leu Asn Trp Cys Val Gln Ile Ala Lys Gly Met Asn Tyr
545                 550                 555                 560
Leu Glu Asp Arg Arg Leu Val His Arg Asp Leu Ala Ala Arg Asn Val
                565                 570                 575
Leu Val Lys Thr Pro Gln His Val Lys Ile Thr Asp Phe Gly Leu Ala
            580                 585                 590
Lys Leu Leu Gly Ala Glu Glu Lys Glu Tyr His Ala Glu Gly Gly Lys
            595                 600                 605
Val Pro Ile Lys Trp Met Ala Leu Glu Ser Ile Leu His Arg Ile Tyr
            610                 615                 620
Thr His Gln Ser Asp Val Trp Ser Tyr Gly Val Thr Val Trp Glu Leu
625                 630                 635                 640
Met Thr Phe Gly Ser Lys Pro Tyr Asp Gly Ile Pro Ala Ser Glu Ile
                645                 650                 655
Ser Ser Ile Leu Glu Lys Gly Glu Arg Leu Pro Gln Pro Pro Ile Cys
            660                 665                 670
Thr Ile Asp Val Tyr Met Ile Met Val Lys Cys Trp Met Ile Asp Ala
            675                 680                 685
Asp Ser Arg Pro Lys Phe Arg Glu Leu Ile Ile Glu Phe Ser Lys Met
            690                 695                 700
Ala Arg Asp Pro Gln Arg Tyr Leu Val Ile Gln Gly Asp Glu Arg Met
705                 710                 715                 720
His Leu Pro Ser Pro Thr Asp Ser Asn Phe Tyr Arg Ala Leu Met Asp
                725                 730                 735
Glu Glu Asp Met Asp Asp Val Val Asp Ala Asp Glu Tyr Leu Ile Pro
            740                 745                 750
Gln Gln Gly Phe Phe Ser Ser Pro Ser Thr Ser Arg Thr Pro Leu Leu
            755                 760                 765
Ser Ser Leu Ser Ala Thr Ser Asn Asn Ser Thr Val Ala Cys Ile Asp
            770                 775                 780
Arg Asn Gly Leu Gln Ser Cys Pro Ile Lys Glu Asp Ser Phe Leu Gln
785                 790                 795                 800
Arg Tyr Ser Ser Asp Pro Thr Gly Ala Leu Thr Glu Asp Ser Ile Asp
                805                 810                 815
Asp Thr Phe Leu Pro Val Pro Glu Tyr Ile Asn Gln Ser Val Pro Lys
            820                 825                 830
Arg Pro Ala Gly Ser Val Gln Asn Pro Val Tyr His Asn Gln Pro Leu
            835                 840                 845
Asn Pro Ala Pro Ser Arg Asp Pro His Tyr Gln Asp Pro His Ser Thr
            850                 855                 860
Ala Val Gly Asn Pro Glu Tyr Leu Asn Thr Val Gln Pro Thr Cys Val
865                 870                 875                 880
Asn Ser Thr Phe Asp Ser Pro Ala His Trp Ala Gln Lys Gly Ser His
                885                 890                 895
Gln Ile Ser Leu Asp Asn Pro Asp Tyr Gln Gln Asp Phe Phe Pro Lys
            900                 905                 910
Glu Ala Lys Pro Asn Gly Ile Phe Lys Gly Ser Thr Ala Glu Asn Ala
            915                 920                 925
```

```
Glu Tyr Leu Arg Val Ala Pro Gln Ser Ser Glu Phe Ile Gly Ala
930                 935                 940
```